United States Patent [19]
Kuhle et al.

[11] 3,962,306
[45] June 8, 1976

[54] SULFONYLOXYPHENYLUREA COMPOUNDS AND HERBICIDAL COMPOSITIONS

[75] Inventors: Engelbert Kühle, Bergisch-Gladbach; Erich Klauke, Odenthal-Hahnenberg; Ludwig Eue, Cologne, all of Germany

[73] Assignee: Bayer Aktiengesellschaft, Leverkusen, Germany

[22] Filed: June 14, 1974

[21] Appl. No.: 479,389

[30] Foreign Application Priority Data

July 7, 1973 Germany............................ 2334607

[52] U.S. Cl.............................. 260/456 A; 71/103
[51] Int. Cl.$^2$........................................ C07C 143/68
[58] Field of Search.................... 260/456 A; 71/103

[56] References Cited
UNITED STATES PATENTS

| | | | |
|---|---|---|---|
| 3,326,663 | 6/1967 | Soloway et al.......................... | 71/2.6 |
| 3,576,872 | 4/1971 | Singhal.................................. | 71/103 |
| 3,687,998 | 8/1972 | Trepka.................................. | 260/456 A |

Primary Examiner—James O. Thomas, Jr.
Assistant Examiner—Nicky Chan
Attorney, Agent, or Firm—Burgess, Dinklage & Sprung

[57] ABSTRACT

New sulfonyloxyphenylureas of the formula

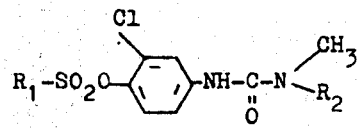

in which
  $R_1$ is alkyl, haloalkyl, phenyl, phenyl substituted with at least one of alkyl, halo-substituted and trifluoromethyl or dialkylamino, and
  $R_2$ is hydrogen, alkyl of from 1 to 4 carbon atoms, or methoxy
are outstandingly effective herbicides displaying particularly selective action.

2 Claims, No Drawings

SULFONYLOXYPHENYLUREA COMPOUNDS AND HERBICIDAL COMPOSITIONS

The present invention relates to certain new sulfonyloxyphenylurea compounds, to herbicidal compositions containing them, and to their use as herbicides.

It is known from U.S. Pat. No. 3,383,195 that N-(3-dimethylamino-sulfonyloxyphenyl)-N',N'-dimethylurea can be used as a herbicide. However, this compound does not show a satisfactory action if low amounts are used.

The present invention provides, as new compounds, sulfonyloxyphenylureas of the formula

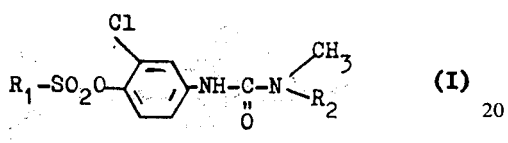

in which
  $R_1$ is alkyl, haloalkyl, phenyl, phenyl substituted with at least one of alkyl, halosubstituted and trifluoromethyl or dialkylamino, and
  $R_2$ is hydrogen, alkyl of from 1 to 4 carbon atoms, or methoxy.

The compounds of formula (I) have been found to display very good herbicidal properties. Surprisingly, the sulfonyloxyphenylureas according to the present invention display a substantially greater herbicidal action than the known compound N-(3-dimethylamino-sulfonyloxyphenyl)-N',N'-dimethylurea. The active compounds according to the present invention thus represent an enrichment of the art.

Preferably $R_1$ is alkyl of from 1 to 4 carbon atoms, chloroalkyl of from 1 to 4 carbon atoms, optionally methyl-substituted, chlorine-substituted or trifluoromethyl-substituted phenyl, or dialkylamino of from 2 to 4 carbon atoms, and $R_2$ is hydrogen, methyl or methoxy.

The present invention also provides a process for the preparation of a sulfonyloxyphenylurea of formula (I), in which an isocyanate of the formula

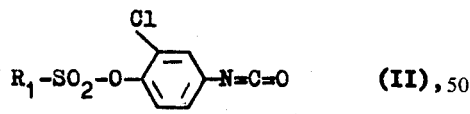

in which
  $R_1$ has the above-mentioned meaning, is reacted with an amine of the formula

in which
  $R_2$ has the above-mentioned meaning, optionally in the presence of a diluent.

If 3-chloro-4-methylsulfonyloxy-phenylisocyanate and dimethylamine are used as starting compounds, the course of the reaction can be represented by the following equation:

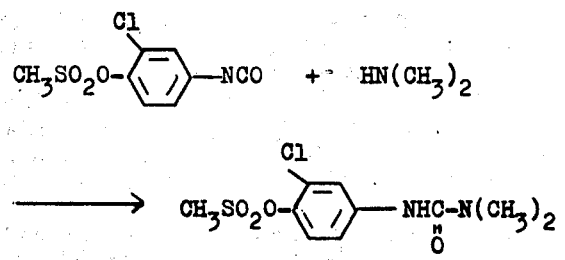

The isocyanates (II) used as starting compounds have not previously been described in the literature. However, they can be prepared in a simple manner from known intermediates, by reacting, in a first stage, 2-chloro-4-nitrophenol of the formula

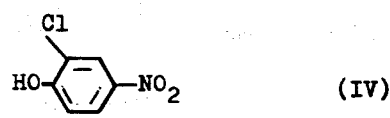

with sulfonic acid chlorides of the formula

in which
  $R_1$ has the above-mentioned meaning, optionally in the presence of a solvent, for example an ether such as dioxane, and optionally in the presence of an acid-binding agent, for example a tertiary amine such as triethylamine, and catalytically hydrating the resulting 4-sulfonyloxynitrobenzenes of the formula

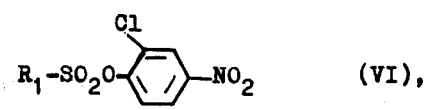

in which
  $R_1$ has the above-mentioned meaning, in a second stage, for example using Raney nickel, and subsequently, in a third stage, converting the resulting anilines of the formula

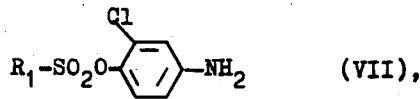

in which
  $R_1$ has the above-mentioned meaning, in the usual manner, by phosgenation, into the isocyanates (II) (see also the preparative examples herein).

The following may be mentioned as examples of isocyanates of formula (II): 3-chloro-4-ethylsulfonyloxy-phenylisocyanate, 3-chloro-4-n-butylsulfonyloxy-phenylisocyanate, 3-chloro-4-N,N-diethylaminosulfonyloxy-phenylisocyanate, 3-chloro-4-(3-chlorophenylsulfonyloxy)-phenylisocyanate, 3-chloro-4-(4-trifluoromethylphenyl-sulfonyloxy)-phenylisocyanate and 3-chloro-4-(4-chloro-3-trifluoromethylphenyl-sulfonyloxy)-phenylisocyanate.

The amines of formula (III) are known. The following may be mentioned as examples thereof: methylamine, dimethylamine, methylethylamine, methylbutylamine, and O,N-dimethylhydroxylamine.

Diluents which can be used are water and all inert organic solvents, especially ethers, such as dioxane, hydrocarbons, such as benzene, chlorinated hydrocarbons, such as chlorobenzene, and ketones, such as acetone.

The reaction temperatures can be varied over a fairly wide range: in general, the reaction is carried out at from 10° to 80°C, preferably at from 20° to 50°C.

In carrying out the process of the present invention, approximately equimolar amounts of isocyanate (II) and amine (III) are preferably employed, although an excess of amine does no harm. Working up is effected in the usual manner.

The preparation of the compounds of the present invention is illustrated in the following preparative examples:

EXAMPLE 1

Preparation of N-(3-chloro-4-methylsulfonyloxyphenyl)-N',N'-dimethylurea

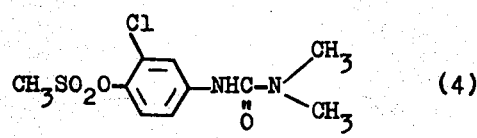
(4)

120 g of dimethylamine were introduced into a solution of 620 g of 3-chloro-4-methylsulfonyloxyphenylisocyanate (alternative name: methanesulfonic acid 2-chloro-4-isocyanatophenyl ester) in 2.5 liters of chlorobenzene at a temperature of 5°–22°C, whilst cooling. The crystals which thereupon formed were filtered off and dried. Yield: 714 g of N-(3-chloro-4-methylsulfonyloxyphenyl)-N',N'-dimethylurea, of melting point 130°–132°C.

EXAMPLE 2

Preparation of N-(3-chloro-4-chloromethylsulfonyloxy-phenyl)-N',N'-dimethylurea

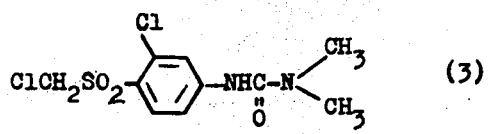
(3)

20 g of 3-chloro-4-chloromethylsulfonyloxyphenylisocyanate (alternative name: chloromethanesulfonic acid 2-chloro-4-isocyanato-phenyl ester) were dissolved in 100 ml of acetone and 10 ml of a 45% strength dimethylamine solution were added, whilst cooling. After addition of water, N-(3-chloro-4-chloromethylsulfonyloxy-phenyl)-N,N'-dimethylurea precipitated: it was filtered off and dried.

Yield: 22 g; melting point 133°C.

The compounds listed in Table 1 which follows can be prepared analogously:

Table 1

| Example No. | Active compound No. | Structural formula | Melting point (°C) |
|---|---|---|---|
| 3 | (1) | (CH₃)₂N-SO₂O-⟨Cl⟩-NHC(O)-N(CH₃)₂ | 145 |
| 4 | (2) | (CH₃)₂N-SO₂O-⟨Cl⟩-NH-C(O)-NH-CH₃ | 172–174 |
| 5 | (5) | ⟨⟩-SO₂-O-⟨Cl⟩-NHCON(CH₃)₂ | 145–147 |
| 6 | (7) | Cl-⟨⟩-SO₂O-⟨Cl⟩-NHCON(CH₃)₂ | 148–149 |
| 7 | (8) | Cl-⟨Cl⟩-SO₂O-⟨Cl⟩-NHCON(CH₃)₂ | viscous oil |
| 8 | (9) | ⟨F₃C⟩-SO₂O-⟨Cl⟩-NHCON(CH₃)₂ | 116–117 |

| Example No. | Active compound No. | Structural formula | Melting point (°C) |
|---|---|---|---|
| 9 | (6) | 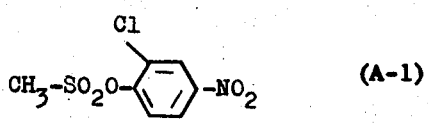 | 87 |

EXAMPLES OF THE PREPARATION OF THE STARTING COMPOUNDS

A. Preparation of 3-chloro-4-methylsulfonyloxy-nitrobenzene (alternative name: methanesulfonic acid 2-chloro-4-nitro phenyl ester):

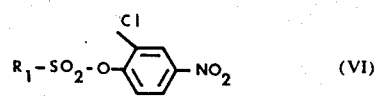 (A-1)

970 ml of triethylamine were added dropwise over the course of 1 hour to a solution of 1,150 g of 2-chloro-4-nitrophenol and 760 g of methanesulfonyl chloride in 4.5 liters of dioxane, at room temperature. In the course thereof, the temperature rose to 62°C. The mixture was stirred for some time and about 7 liters of water were added. Hereupon the reaction product precipitated in the form of an oil which crystallized slowly. After recrystallization from alcohol, 1,506 g of the above product, of melting point 77°–79°C, were obtained.

The following nitrobenzene derivatives could be prepared analogously:

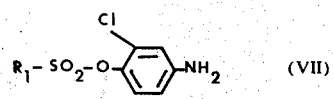 (VI)

| Example No | $R_1$ | Melting point (°C) or refractive index |
|---|---|---|
| (A-2) | Cl—CH₂— | 76–77° |
| (A-3) | (CH₃)₂N— | 78–80° |
| (A-4) | ⟨phenyl⟩ | 107° |
| (A-5) | Cl-⟨phenyl⟩ | 103° |
| (A-6) | Cl-⟨phenyl⟩-Cl | 83–84° |
| (A-7) | F₃C-⟨phenyl⟩ | $n_D^{20} = 1.5470$ |

B. Preparation of 3-chloro-4-methylsulfonyloxy-aniline (alternative name: methanesulfonic acid 2-chloro-4-amino phenyl ester):

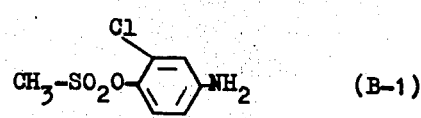 (B-1)

1,506 g of 3-chloro-4-methylsulfonyloxy-nitrobenzene (A-1) were dissolved in 4 liters of dioxane and hydrogenated catalytically in the presence of Raney nickel at 30°C. When the absorption of hydrogen had ceased, the catalyst was filtered off and the filtrate was introduced into about 12 liters of ice-water. The crystals which thereupon resulted were filtered off and dried. Yield: 1,157 g; melting point 81°–83°C.

The following anilines could be prepared analogously:

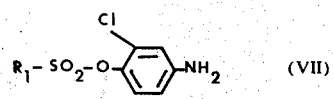 (VII)

| Example No. | $R_1$ | Melting point (°C) |
|---|---|---|
| (B-2) | Cl—CH₂— | oil-like |
| (B-3) | (CH₃)₂N— | 67 |
| (B-4) | ⟨phenyl⟩ | 102–103 |
| (B-5) | Cl-⟨phenyl⟩ | 159–161 |
| (B-6) | Cl-⟨phenyl⟩-Cl | 81–83 |
| (B-7) | F₃C-⟨phenyl⟩ | 85–87 |

C. Preparation of 3-chloro-4-methylsulfonyloxy-phenylisocyanate (alternative name: methanesulfonic acid 2-chloro-4-isocyanatophenyl ester):

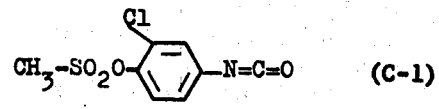 (C-1)

A hot solution of 578 g of 3-chloro-4-methylsulfonyloxyaniline (B-1) in 700 ml of chlorobenzene was added dropwise over the course of 1 hour to a solution of 320 g of phosgene (COCl₂) in 1.5 liters of chlorobenzene at 2°–20°C. The batch was heated gradually, whilst continuing the phosgenation. Solution occurred at about 110°–120°C. The mixture was heated for some hours longer and was concentrated in vacuo. About 600 g of the isocyanate of melting point 65°–67°C were obtained.

The following isocyanates could be prepared analogously:

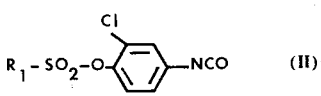

| Example No. | R₁ | Melting point (°C) or refractive index |
| --- | --- | --- |
| (C-2) | Cl—CH₂— | 52–53° |
| (C-3) | (CH₃)₂N— | 53° |
| (C-4) | C₆H₅— (phenyl) | 87–89° |
| (C-5) | Cl-C₆H₄— (4-chlorophenyl) | 108–110° |
| (C-6) | Cl₂-C₆H₃— (dichlorophenyl) | 92° |
| (C-7) | F₃C-C₆H₄— (trifluoromethylphenyl) | $n_D^{20}$ = 1.5450 |

The active compounds according to the invention display strong herbicidal properties. They can be used for destroying weeds.

Weeds in the broadest sense are plants which grow in crops or in other locations where they are undesired. Whether the active compounds according to the invention act as total herbicides or selective herbicides depends essentially on the amount used.

The compounds according to the invention can be used, for example, in the case of the following plants: dicotyledons, such as mustard (Sinapis), cress (Lepidium), cleavers (Galium), chickweed (Stellaria), camomile (Matricaria), gallant soldier (Galinsoga), goosefoot (Chenopodium), annual nettle (Urtica), groundsel (Senecio), cotton (Gossypium), beets (Beta), carrots (Daucus), beans (Phaseolus), potatoes (Solanum) and coffee (Coffea); monocotyledons, such as timothy (Phleum), bluegrass (Poa), fescue (Festuca), goosegrass (Eleusine), foxtail (Setaria), ryegrass (Lolium), cheat (Bromus), barnyard grass (Echinochloa), corn (Zea), rice (Oryza), oats (Avena), barley (Hordeum), wheat (Triticum), millet (Panicum) and sugar cane (Saccharum).

The active compounds according to the invention are particularly suitable for the selective combating of weeds in cotton, cereals, corn and carrots.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds according to the invention can be present in the formulations as a mixture with other active compounds.

In general, the formulations contain from 0.1 to 95 percent by weight of active compound, preferably from 0.5 to 90 percent by weight.

The active compounds can be used as such or in the form of their formulations or the application forms prepared therefrom, such as ready-to-use solutions, emulsions, suspensions, powders, pastes and granules. They may be used in the customary manner, for example by watering, spraying, atomizing, sprinkling or dusting.

They can be used either in the post-emergence process or in the pre-emergence process; they are preferably used after emergence of the plants.

The amount of active compound employed can vary within fairly wide limits. It depends essentially on the nature of the desired effect. In general, the amounts used are from 0.1 to 20 kg/ha, preferably from 0.2 to 10 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier. The present invention further provides means of obtaining crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The herbicidal activity of the compound of this invention is illustrated in the following test examples:

EXAMPLE A

Post-emergence test

Solvent: 5 parts by weight of acetone

Emulsifier: 1 part of weight of alkylaryl polyglycol ether

To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound so that the amounts of active compound per unit area indicated in the table were applied. The amount of water used was 2,000 l/ha. After three weeks, the degree of damage to the plants was determined and characterized by the values 0–5, which had the following meaning:

0—no effect
1—a few slightly burnt spots
2—marked damage to leaves
3—some leaves and parts of stalks partially dead
4—plant partially destroyed
5—plant completely dead.

The active compounds, the amounts used and the results can be seen from Table A. The active compounds are identified therein by numbers which are correlated with the respective formulas in a list given after Table A.

Table A

| Active compound No. | Amount of active compound used kg/ha | Cheno-podium | Sina-pis | Galin-soga | Stella-ria | Urtica | Matri-caria | Carrots | Cotton | Wheat |
|---|---|---|---|---|---|---|---|---|---|---|
| Comparison agent A (known) | 1 | 1 | 5 | 2 | 1 | 2 | 2 | 0 | 2 | 1 |
|  | 0.5 | 1 | 5 | 1 | 0 | 1 | 0 | 0 | 1 | 0 |
| (1) | 1 | 5 | 5 | 5 | 5 | 5 | 5 | 5 | 1 | 3 |
|  | 0.5 | 5 | 5 | 5 | 5 | 5 | 4 | 3 | 0 | 2 |
| (2) | 1 | 4–5 | 5 | 3 | 4 | 5 | 3 | 3 | 1 | 1 |
|  | 0.5 | 4 | 5 | 1 | 3 | 2 | 1 | 2 | 0 | 0 |
| (3) | 1 | 5 | 5 | 3 | 5 | 5 | 4 | 2 | 1 | 3 |
|  | 0.5 | 4–5 | 5 | 2 | 3 | 4 | 3 | 2 | 0 | 2 |
| (4) | 1 | 4–5 | 5 | 5 | 4 | 5 | 5 | 4 | 2 | 2 |
|  | 0.5 | 4–5 | 5 | 4 | 4 | 5 | 4 | 3 | 2 | 1 |
| (5) | 1 | 5 | 5 | 3 | 3 | 3 | 2 | 0 | 2 | 0 |
|  | 0.5 | 4 | 5 | 2 | 2 | 3 | 1 | 0 | 2 | 0 |
| (6) | 1 | 5 | 5 | 2 | 4 | 4–5 | 3 | 0 | 2 | 3 |
|  | 0.5 | 4–5 | 5 | 2 | 3 | 4 | 2 | 0 | 1 | 2 |

List of active compounds

Comparison agent A (US Patent Specification 3,383,195) 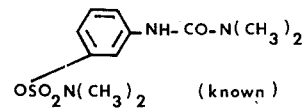 (known)

No.(1) = 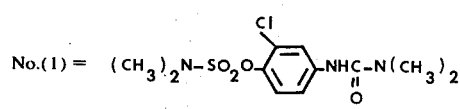

No.(2) = 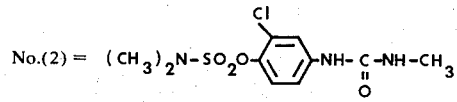

No.(3) = 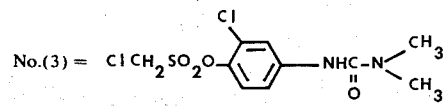

List of active compounds -continued

No.(4) = 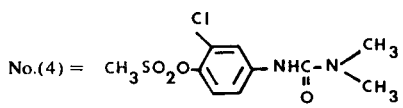

No.(5) = 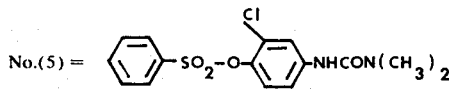

No.(6) = 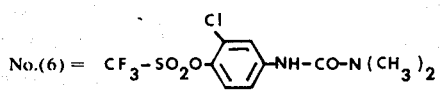

It will be understood that the specification and examples are illustrative but not limitative of the present invention and that other embodiments within the spirit and scope of the invention will suggest themselves to those skilled in the art.

What is claimed is:

1. N-(3-chloro-4-chloromethylsulfonyloxy-phenyl)-N',N'-dimethylurea.
2. N-(3-chloro-4-methylsulfonyloxy-phenyl)-N',N'-dimethylurea.